United States Patent
Kappel et al.

(10) Patent No.: US 11,484,686 B2
(45) Date of Patent: Nov. 1, 2022

(54) MEDICAL DEVICES HAVING RELEASABLE COUPLING

(71) Applicant: Boston Scientific Scimed, Inc., Maple Grove, MN (US)

(72) Inventors: Gary Kappel, Acton, MA (US); Ra Nam, Lawrence, MA (US); Naroun Suon, Lawrence, MA (US); Dan Bacon, Fitchburg, MA (US); Paul Smith, Smithfield, RI (US); John Golden, Norton, MA (US); Barry Weitzner, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 328 days.

(21) Appl. No.: 16/752,711

(22) Filed: Jan. 27, 2020

(65) Prior Publication Data

US 2020/0155799 A1    May 21, 2020

Related U.S. Application Data

(63) Continuation of application No. 15/660,623, filed on Jul. 26, 2017, now Pat. No. 10,576,243, which is a
(Continued)

(51) Int. Cl.
*A61M 37/00* (2006.01)
*A61M 25/00* (2006.01)
(Continued)

(52) U.S. Cl.
CPC ..... *A61M 25/0043* (2013.01); *A61B 17/2909* (2013.01); *A61M 25/0009* (2013.01);
(Continued)

(58) Field of Classification Search
CPC .......... A61M 25/0043; A61M 25/0133; A61B 17/2909; A61B 2017/0046; A61B 2017/003; A61B 2017/00323
See application file for complete search history.

(56) References Cited

U.S. PATENT DOCUMENTS

| 4,539,976 A | 9/1985 | Sharpe |
| 4,590,936 A | 5/1986 | Straub et al. |

(Continued)

FOREIGN PATENT DOCUMENTS

| EP | 0 316 816 B1 | 6/1993 |
| JP | 6-343599 A | 12/1994 |

(Continued)

OTHER PUBLICATIONS

International Search Report and Written Opinion issued in International Application No. PCT/US2012/022837 (Publication No. WO 2012/106187); dated Jun. 22, 2012.
(Continued)

*Primary Examiner* — Laura A Bouchelle
(74) *Attorney, Agent, or Firm* — Bookoff McAndrews, PLLC

(57) ABSTRACT

This invention is directed to a medical device having a longitudinal axis, and including a handle and a catheter. The handle can include a body having a proximal end and a distal end, an actuator moveably coupled to the body, and a handle control member coupled to the actuator, wherein the actuator can be configured to move relative to the body to move the handle control member. The catheter can include a shaft having a proximal end and a distal end, wherein the proximal end of the shaft and the distal end of the body can be configured for releasable coupling. The catheter can also include a steering section located along the shaft and a catheter control member coupled to the steering section, wherein the catheter control member can be configured to
(Continued)

move relative to the shaft to move the steering section relative to the longitudinal axis. The medical device can also include a securing member configured to move relative to at least one of the handle and the catheter to releasably couple the handle control member to the catheter control member.

18 Claims, 14 Drawing Sheets

Related U.S. Application Data continuation of application No. 14/280,141, filed on May 16, 2014, now Pat. No. 9,757,537, which is a continuation of application No. 13/359,917, filed on Jan. 27, 2012, now Pat. No. 8,777,898.

(60) Provisional application No. 61/438,149, filed on Jan. 31, 2011.

(51) Int. Cl.
*A61B 17/29* (2006.01)
*A61M 25/01* (2006.01)
*A61B 17/00* (2006.01)

(52) U.S. Cl.
CPC .... *A61M 25/0113* (2013.01); *A61M 25/0133* (2013.01); *A61M 25/0136* (2013.01); *A61M 25/0147* (2013.01); *A61B 2017/003* (2013.01); *A61B 2017/0046* (2013.01); *A61B 2017/00323* (2013.01); *A61B 2017/291* (2013.01); *A61B 2017/292* (2013.01); *A61B 2017/2905* (2013.01); *A61B 2017/2929* (2013.01); *Y10T 29/49826* (2015.01)

(56) References Cited

U.S. PATENT DOCUMENTS

| | | | |
|---|---|---|---|
| 4,712,547 A | 12/1987 | Bonnet | |
| 4,763,668 A | 8/1988 | Macek et al. | |
| 5,100,420 A | 3/1992 | Green et al. | |
| 5,318,589 A | 6/1994 | Lichtman | |
| 5,471,992 A | 12/1995 | Banik et al. | |
| 5,496,347 A | 3/1996 | Hashiguchi et al. | |
| 5,584,855 A | 12/1996 | Onik | |
| 5,603,711 A | 2/1997 | Parins et al. | |
| 5,603,723 A | 2/1997 | Aranyi et al. | |
| 5,636,639 A | 6/1997 | Turturro et al. | |
| 5,643,294 A | 7/1997 | Tovey et al. | |
| 5,728,117 A | 3/1998 | Lash | |
| 5,755,732 A | 5/1998 | Green et al. | |
| 5,827,323 A | 10/1998 | Klieman et al. | |
| 5,843,000 A | 12/1998 | Nishioka et al. | |
| 5,846,248 A | 12/1998 | Chu et al. | |
| 5,849,022 A | 12/1998 | Sakashita et al. | |
| 5,860,953 A | 1/1999 | Snoke et al. | |
| 5,876,331 A | 3/1999 | Wu et al. | |
| 5,944,654 A | 8/1999 | Crawford | |
| 5,961,526 A | 10/1999 | Chu et al. | |
| 5,984,939 A | 11/1999 | Yoon | |
| 5,997,547 A | 12/1999 | Nakao et al. | |
| 6,001,114 A | 12/1999 | Ouchi | |
| 6,053,877 A | 4/2000 | Banik et al. | |
| 6,059,719 A | 5/2000 | Yamamoto et al. | |
| 6,066,102 A | 5/2000 | Townsend et al. | |
| 6,113,610 A | 9/2000 | Poncet | |
| 6,142,956 A | 11/2000 | Kortenbach et al. | |
| 6,193,737 B1 | 2/2001 | Ouchi | |
| 6,206,904 B1 | 3/2001 | Ouchi | |
| 6,210,416 B1 | 4/2001 | Chu et al. | |
| 6,755,812 B2 | 6/2004 | Peterson et al. | |
| 6,858,005 B2 | 2/2005 | Ohline et al. | |
| 7,169,167 B2 | 1/2007 | Chu | |
| 8,777,898 B2 * | 7/2014 | Suon | A61M 25/0113 604/95.04 |
| 9,757,357 B2 | 9/2017 | Yuasa et al. | |
| 9,757,537 B2 * | 9/2017 | Suon | A61B 17/2909 |
| 2003/0216759 A1 | 11/2003 | Burbank et al. | |
| 2004/0236316 A1 | 11/2004 | Danitz et al. | |
| 2005/0096694 A1 | 5/2005 | Lee | |
| 2006/0020287 A1 | 1/2006 | Lee et al. | |
| 2006/0052664 A1 | 3/2006 | Julian et al. | |
| 2006/0079873 A1 | 4/2006 | Scopton et al. | |
| 2007/0167677 A1 | 7/2007 | Chu | |
| 2008/0172038 A1 | 7/2008 | Dollar et al. | |
| 2008/0188868 A1 | 8/2008 | Weitzner et al. | |
| 2008/0188890 A1 | 8/2008 | Weitzner et al. | |
| 2008/0287862 A1 | 11/2008 | Weitzner et al. | |
| 2009/0171147 A1 * | 7/2009 | Lee | A61B 17/29 600/137 |
| 2010/0261964 A1 | 10/2010 | Danitz et al. | |
| 2011/0172706 A1 | 7/2011 | Kappel et al. | |
| 2012/0004648 A1 | 1/2012 | Choi et al. | |

FOREIGN PATENT DOCUMENTS

| | | |
|---|---|---|
| WO | WO 97/12557 A1 | 4/1997 |
| WO | WO 02/07611 A2 | 1/2002 |
| WO | WO 2008/083318 A2 | 7/2008 |
| WO | WO 2009/0171147 A1 | 7/2009 |
| WO | WO 2010/101401 A2 | 9/2010 |
| WO | WO 2012/004648 A1 | 1/2012 |

OTHER PUBLICATIONS

International Search Report and Written Opinion issued in International Application No. PCT/US2012/022837, dated Aug. 15, 2013, 13 pages.

* cited by examiner

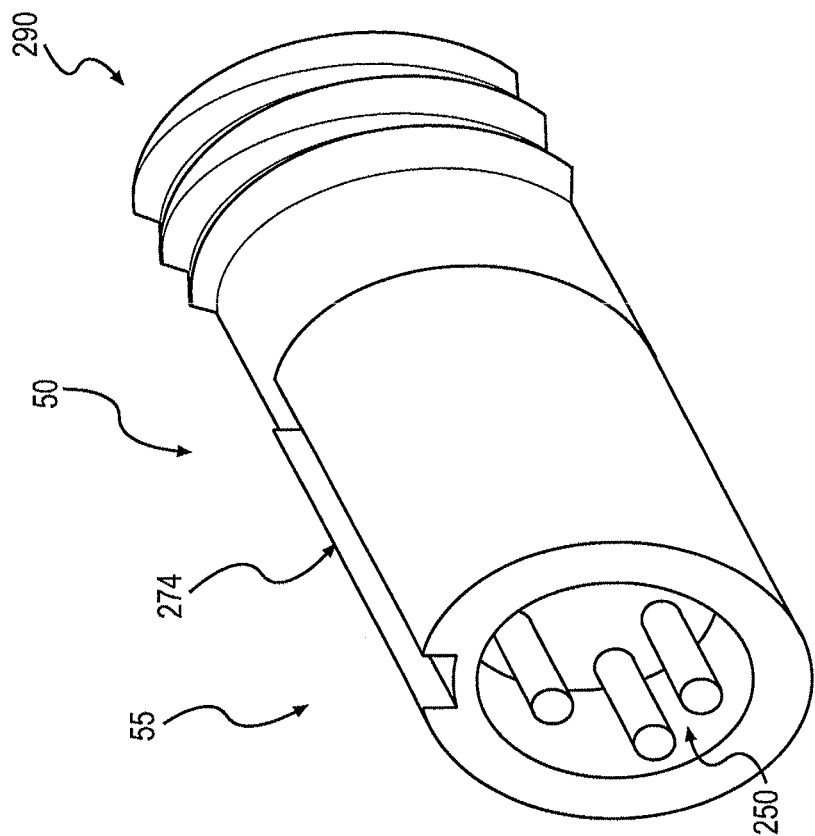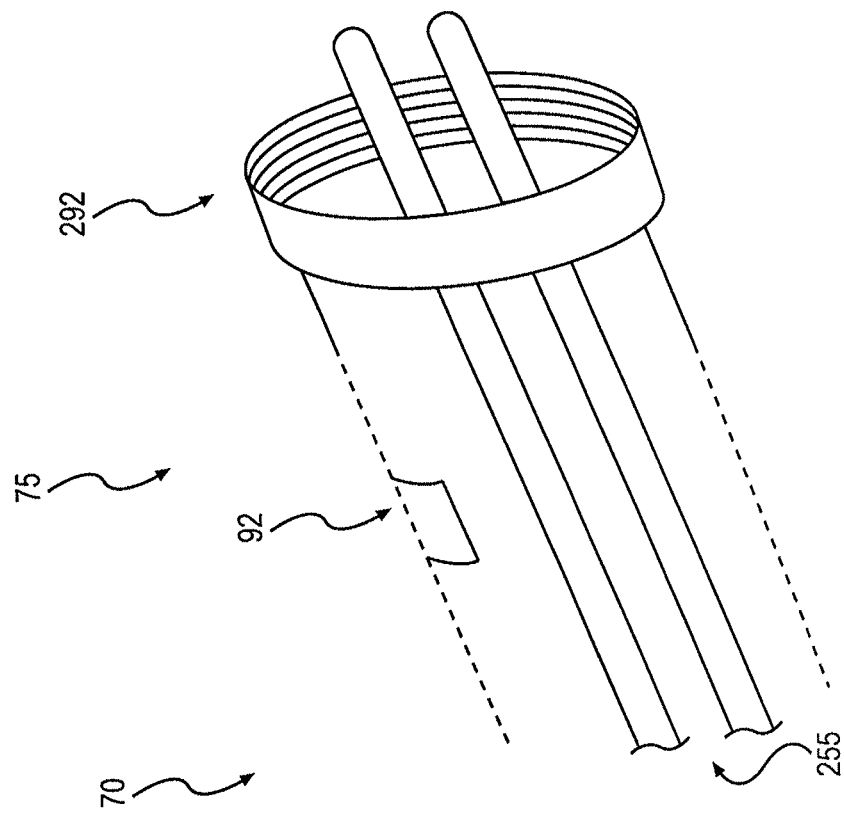
FIG. 5

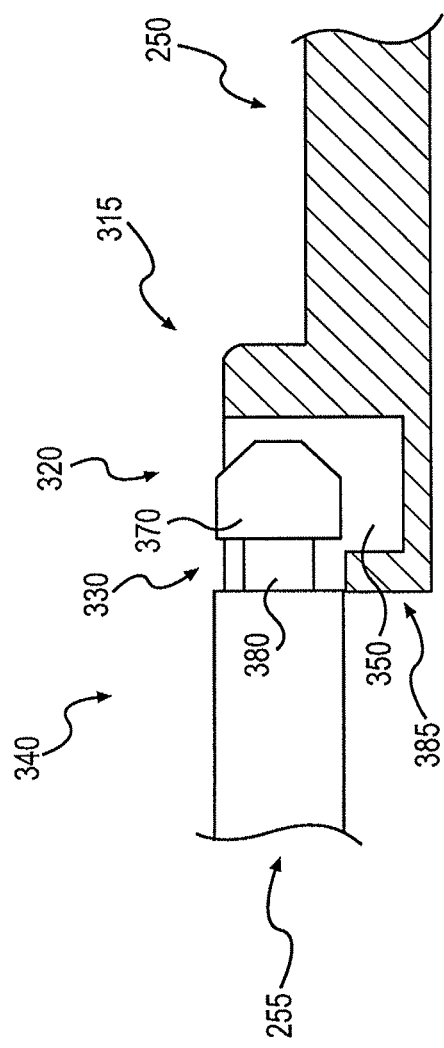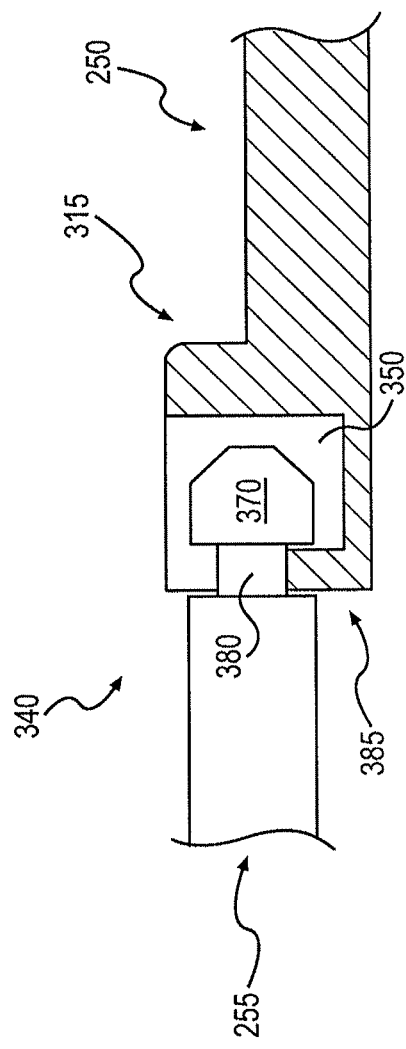

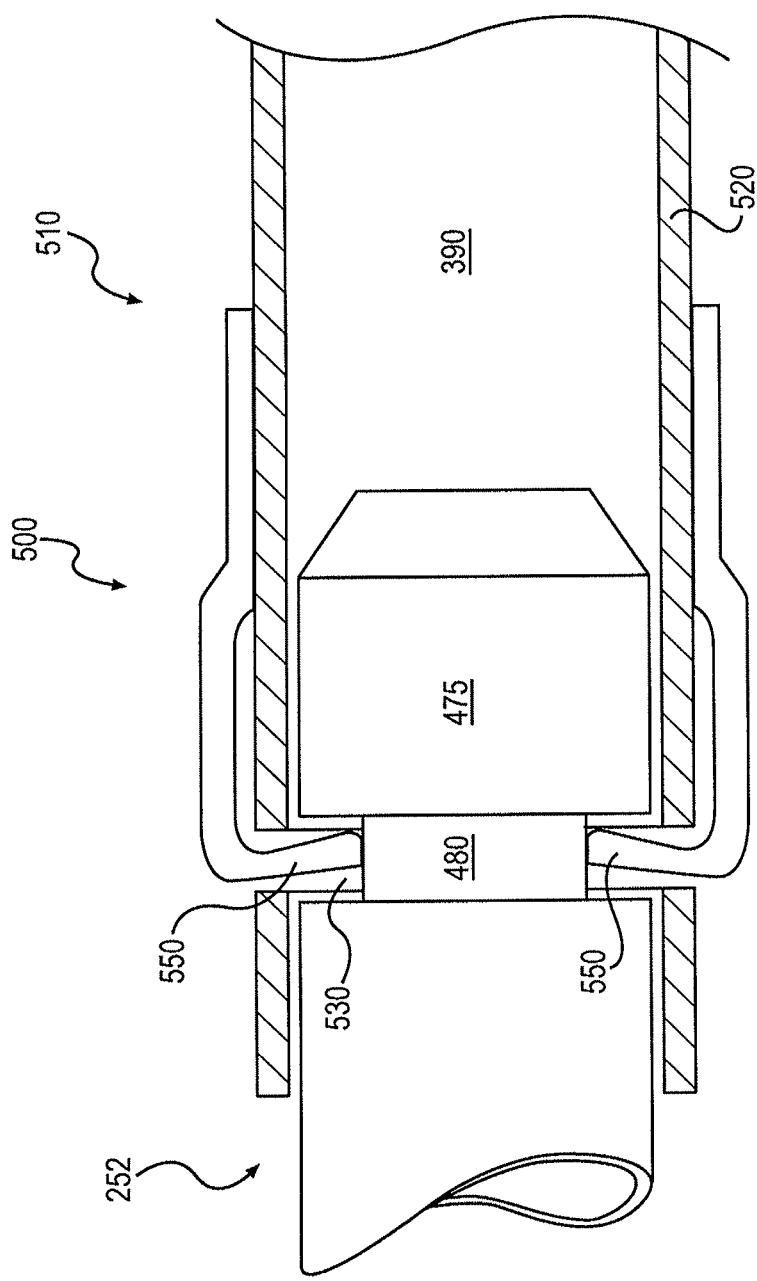

MEDICAL DEVICES HAVING RELEASABLE COUPLING

DESCRIPTION OF THE INVENTION

This application is a continuation of U.S. patent application Ser. No. 15/660,623, filed Jul. 26, 2017, which is a continuation of U.S. patent application Ser. No. 14/280,141, filed May 16, 2014, now U.S. Pat. No. 9,757,537, issued Sep. 12, 2017, which is a continuation of U.S. patent application Ser. No. 13/359,917, filed Jan. 27, 2012, now U.S. Pat. No. 8,777,898, issued Jul. 15, 2014, which claims the benefit of priority from U.S. Provisional Patent Application No. 61/438,149, filed Jan. 31, 2011, each of which is incorporated herein by reference in its entirety.

FIELD OF THE INVENTION

Embodiments of the present invention relate to medical devices. In particular, embodiments of the present invention include medical devices having releasable coupling.

BACKGROUND OF THE INVENTION

Minimally invasive surgical tools, such as endoscopic and laparoscopic devices, can provide access to surgical sites while minimizing patient trauma. Although the growing capabilities of such therapeutic devices allow physicians to perform an increasing variety of surgeries, further refinements are needed to reduce costs associated with such procedures.

Some minimally invasive systems include surgical devices that may be sterilized for reuse. Such devices are usually expensive to manufacture and must be designed to withstand multiple sterilization procedures. Similar disposable devices often have limited performance due to the use of cheaper materials and low-cost manufacturing techniques.

SUMMARY OF THE INVENTION

The medical devices described herein overcome at least some of the limitations of the prior art. One aim of at least certain embodiments of the present invention is to reduce costs by providing a medical device that can include some reusable and some disposable components. For example, a medical device could include a reusable handle and a disposable catheter. The reusable handle could be adapted for use with different types of catheters having different end-effectors.

One aspect of the invention is directed to a medical device having a longitudinal axis, and including a handle and a catheter. The handle can include a body having a proximal end and a distal end, an actuator moveably coupled to the body, and a handle control member coupled to the actuator, wherein the actuator can be configured to move relative to the body to move the handle control member. The catheter can include a shaft having a proximal end and a distal end, wherein the proximal end of the shaft and the distal end of the body can be configured for releasable coupling. The catheter can also include a steering section located along the shaft and a catheter control member coupled to the steering section, wherein the catheter control member can be configured to move relative to the shaft to move the steering section relative to the longitudinal axis. The medical device can also include a securing member configured to move relative to at least one of the handle and the catheter to releasably couple the handle control member to the catheter control member.

According to another aspect, the invention can include a handle configured to releasably couple to a catheter. The handle can include a body configured to releasably couple to the catheter, an actuator moveably coupled to the body and configured to engage a user's hand, and a plurality of handle control members coupled to the actuator, wherein the actuator can be configured to move relative to the body to move at least one of the plurality of handle control members. The handle can also include a securing member configured to move relative to the handle to releasably couple the plurality of handle control members to a plurality of catheter control members.

According to another aspect, the invention can include a catheter configured to releasably couple to a handle. The catheter can include a shaft configured to releasably couple to the handle, a steering section located along the shaft, and a plurality of catheter control members coupled to the steering section, wherein each of the plurality of catheter control members can include a first attachment member and can be configured to move relative to the shaft to move the steering section. The catheter can also include a lumen configured to at least partially maintain coupling between the first attachment member and a corresponding attachment member located on a handle control member.

According to another aspect, the invention can include a method of assembling a medical device. The method can include moving a handle having a handle control member relative to a catheter having a catheter control member in untensioned state, to engage the handle control member with the catheter control member. The method can also include moving a securing member from a first position to a second position to tension the catheter control member and couple the handle control member to the catheter control member.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 5 is a partial cut-away perspective view of a detached device, according to an exemplary embodiment of the invention;

FIG. 7A is a side view of decoupled attachment members, according to an exemplary embodiment of the invention;

FIG. 7B is a side view of coupled attachment members, according to an exemplary embodiment of the invention;

FIG. 11B is a side view of attachment members in a coupled configuration, according to an exemplary embodiment of the invention.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts.

Figure 1:
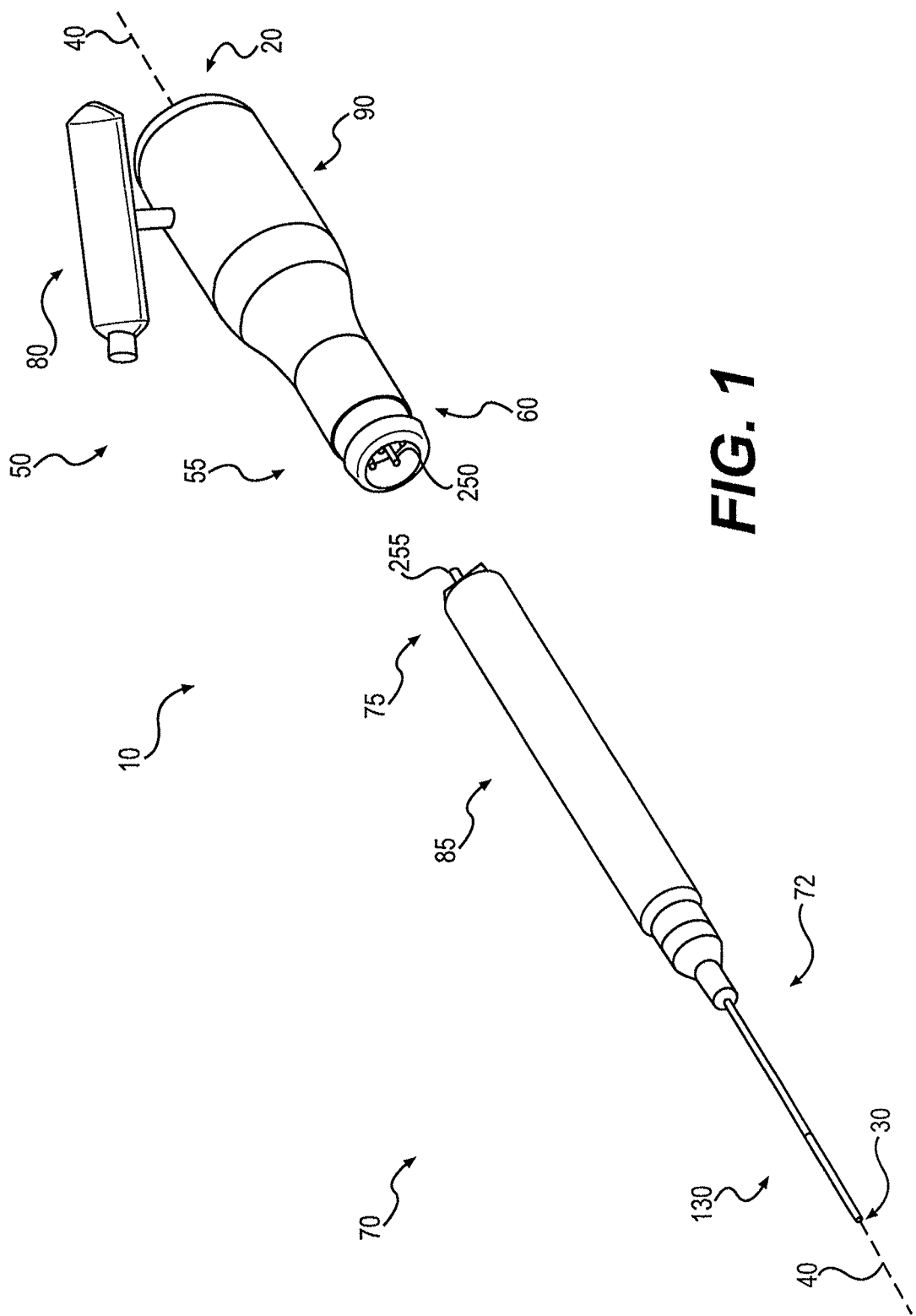
FIG. 1 is perspective view of a device in a detached configuration, according to an exemplary embodiment of the invention.

FIG. 1 depicts a device 10, according to an exemplary embodiment.

Device 10 is shown in a detached configuration, whereby a handle 50 is shown separated from a catheter 70. As described herein, handle 50 and catheter 70 are configured for releasable coupling. Specifically, handle 50 can be attached to catheter 70 to allow handle 50 to control a movement, actuation, and/or operation of catheter 70. Handle 50 can also be detached from catheter 70 so that other catheters 70 may be attached to handle 50.

In some embodiments, handle 50 could be reusable and catheter 70 could be disposable. Multiple catheters 70, having different end-effectors, could be used interchangeably with a single handle 50. Various different catheters 70 could be provided together in kit form, wherein each catheter 70 has a different end-effector.

Device 10 can include a medical device configured for use with a surgical method, including a therapeutic or diagnostic procedure. For example, device 10 can be configured for use with an endoscope, a guide tube, an access catheter, or other type of device configured to access a patient's body. Device 10 may be used for procedures within or adjacent to various body organs, such as, an esophagus, a heart, a stomach, a pelvic area, a bladder, an intestine, or any other portion of a gastrointestinal, urinary, or pulmonary tract.

Device 10 may be configured for insertion into a patient's body through an anatomical opening. In other embodiments, device 10 may be used in natural orifice transluminal endoscopic surgery (NOTES) procedures or single incision laparoscopic surgical (SILS) procedures. Accordingly, device 10 can be shaped and sized for placement into a patient via a body cavity or an incision.

Device 10 can have a proximal end 20, a distal end 30, and a longitudinal axis 40. Handle 50 can include a distal end 55. Catheter 70 can include a proximal end 75. As shown in FIG. 1, distal end 55 of handle 50 can be configured to engage proximal end 75 of catheter 70. Distal end 55 can also be configured to engage another part of catheter 70. Also, another part of handle 50 can be configured to engage to proximal end 75 or another part of catheter 70.

Catheter 70 can be elongate and may include a shaft 72. Shaft 72 can be flexible and may include one or more lumens (not shown). Catheter 70 can also include a rail 65 configured to moveably couple a frame (not shown) to permit movement of device 10 along or about longitudinal axis 40. Catheter 70 can also include a steering section 130.

As shown in FIG. 1, steering section 130 can be located at or near distal end 30. In other embodiments, steering section 130 can be located anywhere along shaft 72, or encompass the entire length of shaft 72. In operation, a user can manipulate steering section 130 to move distal end 30 up, down, left, or right. Handle 50 can be configured to control movement of catheter 70 in one or more directions relative to longitudinal axis 40.

Handle 50 can include a grip 80 moveably coupled to a handle body 90. Grip 80 can be an actuator configured to receive user inputs. For example, grip 80 could be configured to engage a left hand or a right hand of a user. Grip 80 could include a ridge located to separate two adjacent fingers, a surface conforming to part of a human hand, or an aperture configured to receive two or more digits of a user. An exemplary handle is described in U.S. Patent Application Publication No. 2008/0188868, which is incorporated by reference here in its entirety.

Movement of a user's hand may move grip 80 relative to body 90 to move catheter 70. Movement of handle 50 along or about longitudinal axis 40 may move catheter 70 along or about longitudinal axis 40. In other embodiments, handle 50 can include one or more knobs, dials, levers, or other devices configured to control catheter 70.

Handle 50 can be configured to provide direct manual user control of catheter 70. For example, handle 50 can be configured to selectively move catheter 70 using direct manual user movement. In some embodiments, movement or forces can be mechanically transmitted from handle 50 to catheter 70 via one or more control members 250, 255. One or more handle control members 250 may extend within handle 50 and one or more catheter control members 255 may extend within catheter 70. Handle 50 may move one or more control members 250, 255 to move one or more parts of catheter 70.

Control members 250, 255 can include a cable, a wire, a ribbon, or other type of elongate element configured to transfer a movement or a mechanical force. Control members 250, 255 can be configured to transfer tensile force, compressive force, or both tensile and compressive forces. For example, control members 250, 255 could include a metal alloy, braided synthetic thread, coil, or similar flexible material configured to transfer a tensile force. Control members 250, 255 may be sized and shaped depending on load requirements and geometric constraints.

Control members 250, 255 are described herein as including various features and having various functions. One of ordinary skill will also appreciate that these various features and functions are interchangeable between handle control members 250 and catheter control members 255. That is, either handle control member 250 or catheter control member 255 could include one or more features or functions ascribed to a particular control member.

As explained below, handle control members 250 may be releasably coupled to catheter control members 255, wherein each handle control member 250 can be coupled to a corresponding catheter control member 255. In some embodiments, a securing member 60 can be configured to move to releasably couple handle control members 250 and catheter control members 255.

Figure 2:
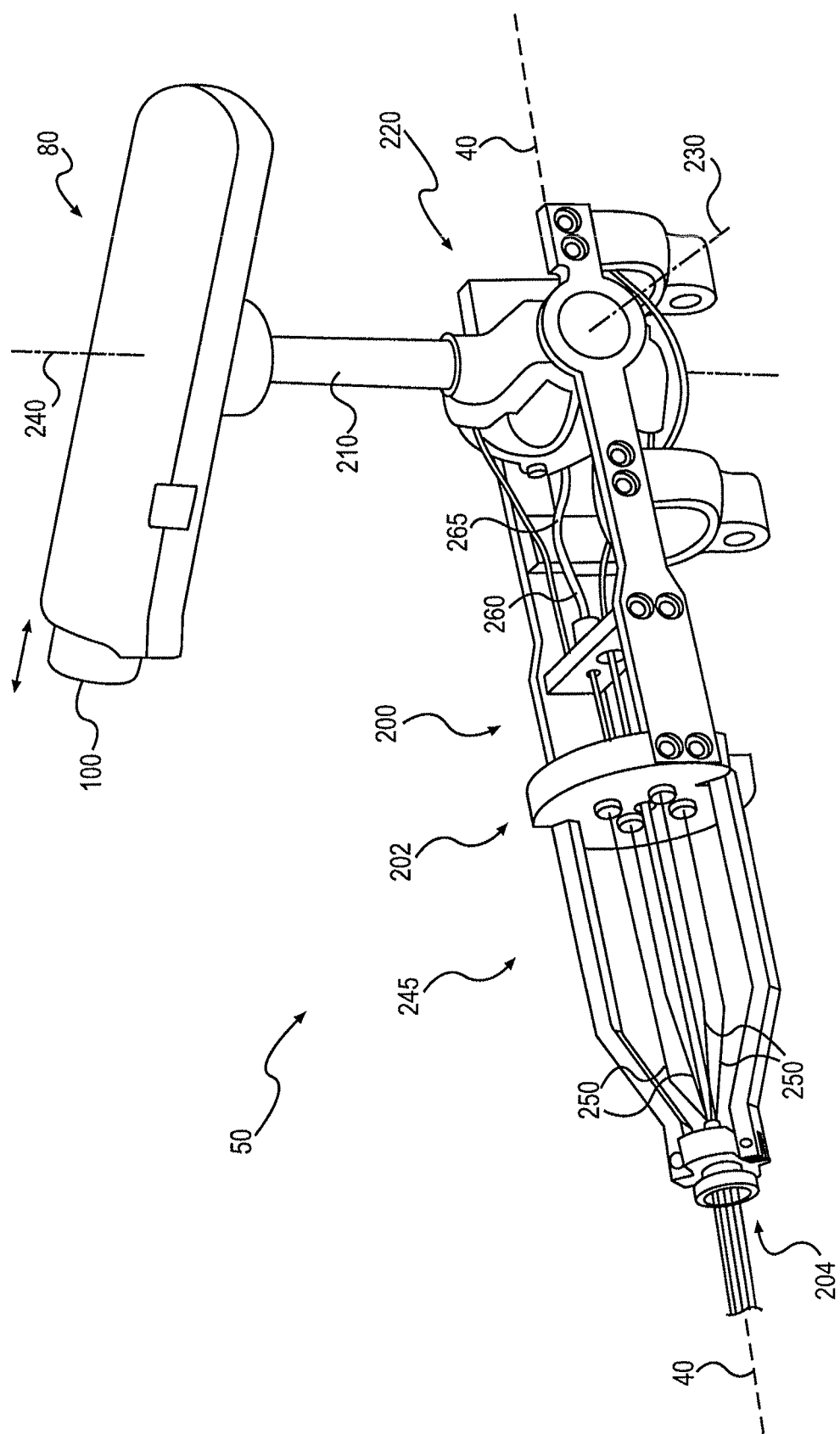
FIG. 2 is a cut-away perspective view of a handle, according to an exemplary embodiment of the invention.

FIG. 2 depicts a cut-away perspective view of handle 50, wherein an outer layer of handle 50 has been removed to reveal a frame 200. As shown, grip 80 can be moveably coupled to frame 200 via a grip shaft 210 and a trunion 220. Grip 80 may also be coupled to frame 200 using a hinge, a flexible member, or other type of moveable coupling.

Grip 80 can be configured for rotational movement about one or more axes relative to frame 200. For example, grip 80 can be rotated forward or backwards by a user about a lateral axis 230 to provide up or down articulation of catheter 70. Grip 80 can be rotated about grip shaft axis 240 to provide left or right articulation of catheter 70. Forward or backward movement of a user's hand along longitudinal axis 40 may move handle 50 and catheter 70 forward or backwards along longitudinal axis 40. In other embodiments, different movements of grip 80 can selectively move catheter 70.

Grip 80 can include a trigger 100 that may be moved to provide actuation of an end-effector located on catheter 70. Trigger 100 can be positioned on grip 80 for control by a user's thumb or for finger control, Trigger 100 could also be located on frame 200.

Handle control members 250 can be coupled to trunion 220, grip 80, grip shaft 210, trigger 100, or similar components such that movement of those components can provide movement of handle control members 250 relative to frame 200, For example, trigger 100 can be coupled to handle control member 250 within grip 80. Such a trigger control member 250 may then pass through grip 80, through grip shaft 210 and through frame 200. Moving trigger 100 can move the trigger control member 250 to selectively actuate an end-effector. Movement of one or more control members 250 can move one or more catheter control members 255 to selectively articulate or actuate catheter 70.

At least part of handle control member 250 can include a Bowden cable 260. Bowden cable 260 can include a sheath 265 surrounding at least part of handle control member 250. Relative movement between sheath 265 and handle control member 250 can transfer compressive or tensile forces. Compressive forces can be transferred through sheath 265 and tensile forces can be transferred through handle control member 250. Tensile forces may also be applied to handle control member 250 by passing control member 250 through part of frame 200, For example, handle control members 250 could pass through a plate 202 or a hub 204, FIG. 3A depicts an end-effector 110 for use with device 10. End-effector 110 is shown in FIG. 3A in three different positions; vertical; forty five degrees relative to vertical; and horizontal. End-effector 110 can be moved as indicated by arrows 125 in various directions relative to longitudinal axis 40 by movement of one or more catheter control members 255 coupled to steering section 130.

Steering section 130 can include a plurality of articulation links 135. Articulation links 135 can be moved relative to adjacent links via a pivot, flexible connection, sliding engagement, bearing, or other type of joint. One or more articulation links 135 can be coupled to one or more catheter control members 255 to control movement of steering section 130.

As shown in FIG. 3A, steering section 130 can be articulated relative to longitudinal axis 40. Although FIG. 3A shows steering section 130 moving about 90 degrees from longitudinal axis 40, steering section 130 may move through a greater or lesser range of angles relative to longitudinal axis 40. Further, steering section 130 could be articulated in multiple directions relative to longitudinal axis 40, such as, for example, in and out of the page.

In some embodiments, end-effector 110 can include a grasper 115 having one or more movable jaw members 120 hingedly attached to catheter 70. Grasper 115 can be configured to grasp tissue. Jaw members 120 may be actuated to move relative to each other. For example, jaw members 120 can be configured to assume an open configuration 135, a closed configuration 140, or any configuration therebetween.

Figure 3B:
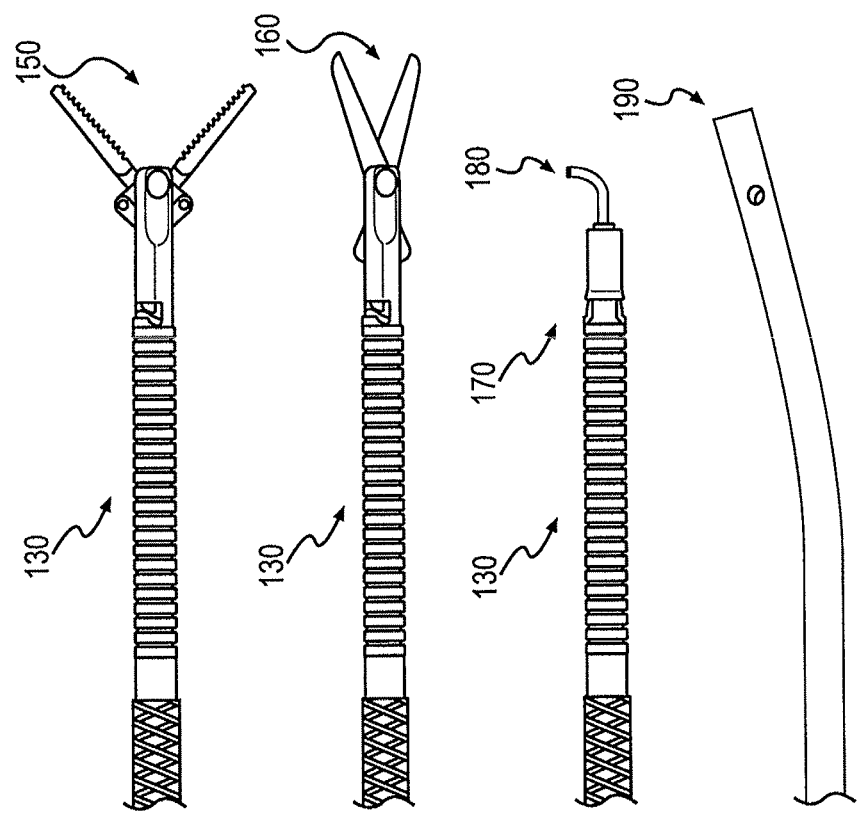
FIG. 3B is a side view of various end-effectors, according to exemplary embodiments of the invention.
Figure 3A:
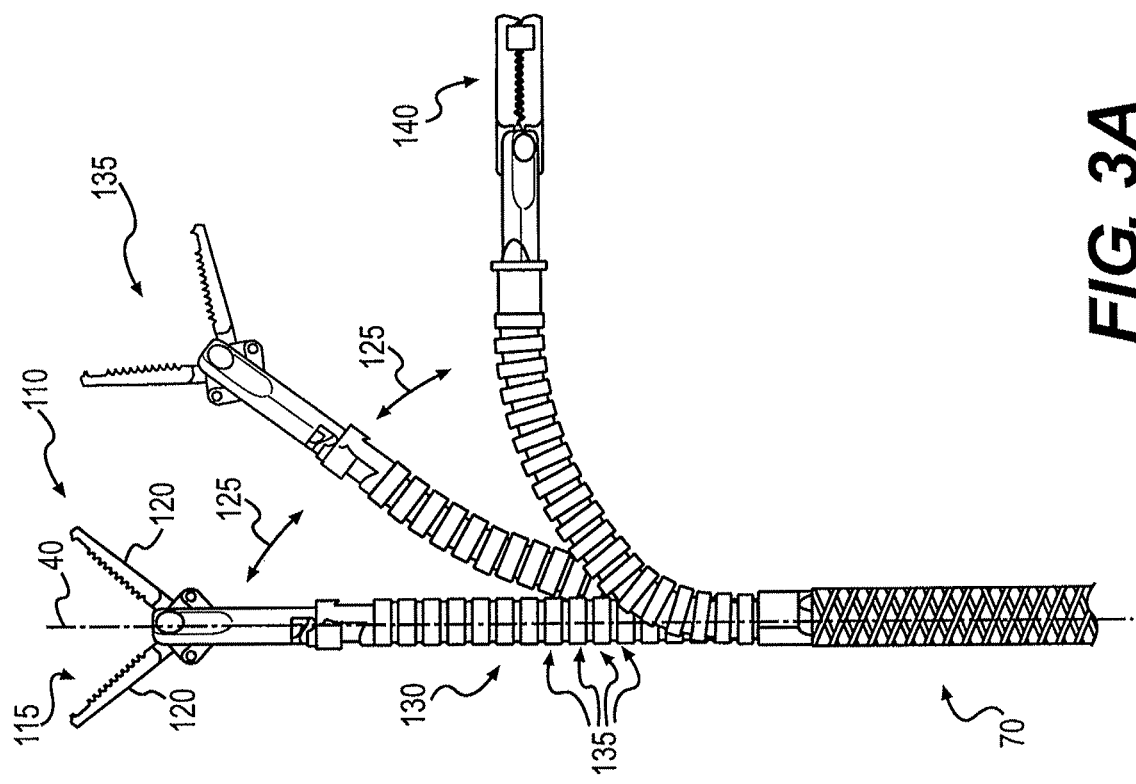
FIG. 3A is a side view of an end-effector articulated in three different positions, according to an exemplary embodiment of the invention.

FIG. 3B depicts various end-effectors configured for use with catheter 70. These and other types of end-effectors may be distally located on catheter 70 and can be articulated or actuated. One or more catheter control members 255 can be moved to control articulation of steering section 130 and one or more different catheter control members 255 can be moved to control actuation of one or more moveable members of end-effector 110.

A dissector 150 and a pair of scissors 160 can be provided. Both dissector 150 and scissors 160 can include multiple catheter control members 255 configured to provide articulation and actuation of both types of end-effectors. End-effector could also include an electrosurgical hook 170, having a hook 180 configured to apply ablative energy to tissue. Electrosurgical hook 170 may require articulation and may not require actuation. Catheter 70 could also include a tube 190 configured to provide suction or irrigation to a region distal of catheter 70. Tube 190 may not require articulation or actuation.

Figure 4A:
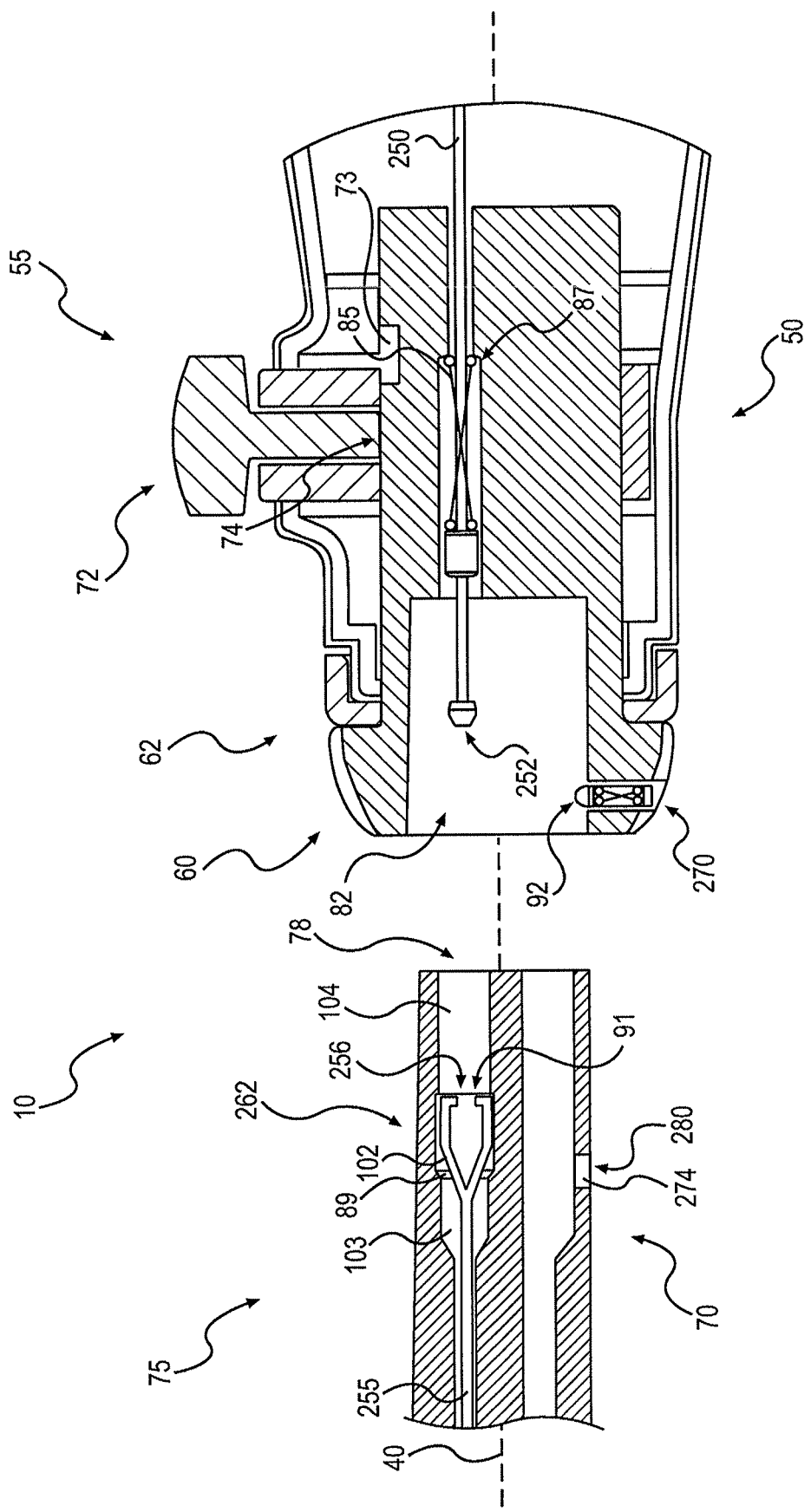
FIG. 4A is a side view of a detached device, according to an exemplary embodiment of the invention.
Figure 4B:
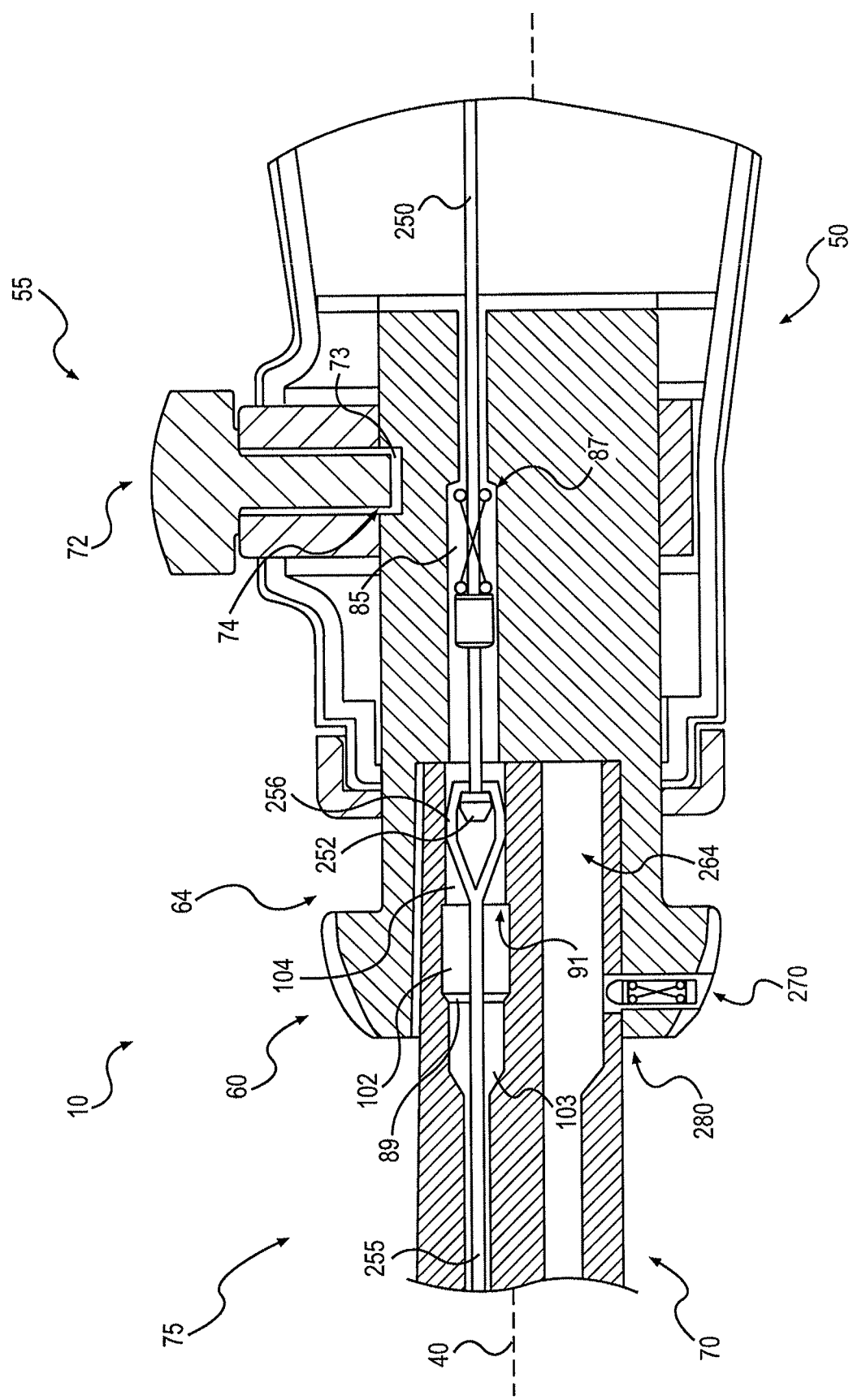
FIG. 4B is a side view of an attached device, according to an exemplary embodiment of the invention.

FIG. 4A is an enlarged cross-sectional side view of device 10 in a detached configuration, whereby handle 50 is decoupled from catheter 70. FIG. 4B shows device 10 as attached, whereby handle 50 is coupled to catheter 70. Handle 50 and catheter 70 can be configured for releasable coupling. For example, distal end 55 of handle 50 and proximal end 75 of catheter 70 can be releasably coupled. Distal end 55 can include a lumen 82 configured to receive proximal end 75. As explained below, handle 50 and catheter 70 could couple using a bayonet connection, a threaded connection, or other type of mechanical coupling.

FIGS. 4A and 4B show securing member 60 as part of distal end 55 of handle 50. Securing member 60 could be part of proximal end 75 of catheter 70 or could connect separately to handle 50 and catheter 70. While handle 50 is shown with one handle control member 250 and catheter 70 is shown with one catheter control member 255, handle 50 and catheter 70 could include multiple control members 250, 255.

Securing member 60 can be moved to releasably couple a plurality of handle control members 250 and a plurality of catheter control member 255. Securing member 60 can be configured to move relative to handle 50 or catheter 70. For example, securing member 60 can move rotationally or longitudinally relative to handle 50. In particular, securing member 60 may move distally from a first position 62 (as shown in FIG. 4A) to a second position 64 (as shown in FIG. 4B). Handle control member 250 may remain in a fixed position relative to handle 50 as securing member 60 is moved from first position 62 to second position 64. Securing member 60 can also move proximally from second position 64 to first position 62. Such movements can couple and decouple handle 50 and catheter 70. Various other types of movement or positioning of securing member 60 are also contemplated, such as, for example, longitudinal and rotational movement.

Control members 250, 255 can be configured for releasable coupling. In some embodiments, control members 250, 255 can each include one or more attachment members configured for releasable coupling. As shown, handle control member 250 can include an attachment member 252 and catheter control member 255 can include a corresponding attachment member 256. In other embodiments, handle control member 250 could include attachment member 256 and catheter control member 255 could include corresponding attachment member 252.

Attachment member 252 and corresponding attachment member 256 can be configured to releasably couple to each other. Various types of attachment members 252, 256 are contemplated. Some may couple using straight-line attachment, such as, for example, as shown in FIGS. 4A and 4B.

In operation, proximal end 75 of catheter 70 may be positioned adjacent to distal end 55 of handle 50. Securing member 60 may initially be in first position 62 such that attachment member 252 can be located within lumen 82, as shown in FIG. 4A, Attachment member 252 and corresponding attachment member 256 may be aligned based on complementary shapes of attachment members 252, 256, complementary shapes of distal end 75 and lumen 82, or one or more alignment features (not shown). For example, a first attachment member 252 could have a first shape configured to couple with only a first attachment member 256, and a second attachment member 252 could have a second shape different to the first shape and configured to couple with only a second attachment member 256.

Proximal end 75 can then be moved proximally within lumen 82 to locate attachment member 252 within corresponding attachment member 256. As distal end 75 moves proximally, a retaining member 85 may be configured to generally maintain a position of attachment member 252 relative to lumen 82. Retaining member 85 may be necessary to ensure that attachment member 252 is not inadvertently moved proximally by the proximal movement of distal end 75. If attachment member 252 is inadvertently moved proximally, attachment members 252, 256 may not properly engage.

In some embodiments, retaining member 85 can be biased to apply a tensile force to attachment member 252 to limit the movement of attachment member 252. The tensile force applied to attachment member 252 may be sufficient to maintain a position of attachment member 252 relative to lumen 82. Such a tensile force should not affect movement of handle control member 250.

Retaining member 85 can include a spring, a button, a lever, a latch, or similar device. Retaining member 85 could be coupled to attachment members 252, 256 or control members 250, 255. For example, one or more retaining members 85 could be configured to retain a position of one or more handle control members 250 relative to handle 50 or a position of one or more catheter control members 255 relative to catheter 70.

Retaining member 85, or similar biasing, can be used for any connection described herein. Such a mechanism may reduce slack and/or lock elements to be connected or disconnected. Various mechanism to tension and lock elements can include hook and loop, ball and slot, tab and hole, or threaded connections.

In some embodiments, proximal movement of retaining member 85 may be limited. For example, securing member 60 could include a stop feature 87 configured to limit proximal movement of retaining member 85. Stop feature 87 could include a ledge, a step, or similar structure.

Control members 250, 255 may initially be provided in an untensioned or a relaxed state. Such a state may reduce forces applied to control members 250, 255 to reduce the likelihood that control member 250, 255 could be stretched during storage, shipping, or sterilization. Various systems may be used to untension or tension one or more control members 250, 255.

In some embodiments, catheter control member 255 may be located in a lumen 103 extending within proximal end 75 of catheter 70. Lumen 103 can be shaped and sized to receive catheter control member 255. Lumen 103 can also include a lumen 102 shaped and sized to receive attachment member 256. Lumen 102 can form part of lumen 103. For example, lumen 102 can be located proximal to lumen 103. Lumen 103 can also be shaped and sized to limit distal movement of attachment member 256.

As shown in FIGS. 4A and 4B, proximal end 75 can include a transition feature 89 located between lumen 103 and lumen 102. Transition feature 89 can include a ledge, a step, or similar structure configured to limit distal movement of attachment member 256. In particular, transition feature 89 may limit distal movement of attachment member 256 as attachment members 252, 256 are coupled together.

Lumen 103 could also include a lumen 104 configured to receive attachment member 256 following coupling of attachment members 252, 256. As shown in FIG. 4B, coupled attachment members 252, 256 can be moved proximally and distally within lumen 104 to permit the transfer to forces or movement between control members 255, 250. Proximal end 75 can also include a transition feature 91 located between lumen 102 and lumen 104. In some embodiments, transition feature 91 can include a slope, a taper, or similar structure configured to permit coupling or decoupling of attachment members 252, 256. Attachment members 252, 256 may further include magnetic or geometric locking parts to enhance connections.

FIG. 4A shows attachment member 256 in an open configuration 262, wherein attachment member 256 can be located within lumen 102. In open configuration 262, attachment member 252 may be moved longitudinally to position attachment member 252 within corresponding attachment member 256. Coupling and decoupling of attachment members 256, 252 may occur by moving attachment members 256, 252 between lumen 102 and lumen 104.

FIG. 4B shows attachment member 256 in closed configuration 264, wherein attachment member 256 can be located within lumen 104. In closed configuration 264, attachment member 252 may be held within corresponding attachment member 256 such that attachment members 252, 256 are coupled to permit transfer of movement or forces between control members 250, 255. Following coupling, movement of control members 250, 255 may move coupled attachment members 252, 256 within lumen 104.

Lumen 102 can also be configured to maintain catheter control member 255 in an untensioned state. For example, attachment member 256 may initially be located within lumen 102. Lumen 102 may be located distal to lumen 104. Moving attachment member 256 proximally from lumen 102 into lumen 104 may function to tension catheter control member 255. Sufficient tension could be applied to ensure appropriate transfer of forces and movement along catheter control member 255.

Attachment member 256 can be biased. For example, attachment member 256 could be biased in open configuration 262 or closed configuration 264. Also, lumen 102 can be configured to maintain attachment member 256 in open configuration 262. For example, lumen 102 could be dimensioned to permit attachment member 256 to assume open configuration 262, as shown in FIG. 4A. Specifically, lumen 102 may have an inner diameter sufficient to permit attachment member 256 to assume open configuration 262.

Once proximal end 75 of catheter 70 is located within lumen 82 of handle 50 and attachment member 252 is located within corresponding attachment member 256, securing member 60 may be moved from first position 62 to second position 64. As shown in FIG. 4B, the movement of securing member 60 to second position 64 may move coupled attachment members 252, 256 into lumen 104.

Lumen 104 can be configured to receive attachment member 256. Lumen 104 can be further configured to provide attachment member 256 in closed configuration 264. For example, lumen 104 may be dimensioned to cause attachment member 256 to assume closed configuration 264. In other embodiments, lumen 104 could include a surface, a protrusion, or other feature configured to provide closed configuration 264. Lumen 104 may apply a compressive force to attachment member 256 to maintain closed configuration 264. Closed configuration 264 can maintain coupling between attachment members 252, 256 by limiting the relative movement between attachment members 252, 256.

In closed configuration 264, attachment members 252, 256 may provide coupling between handle control member 250 and catheter control member 255. This coupling can be released by moving attachment member 256 from lumen 104 to lumen 102. For example, moving securing member 60 from second position 64 (as shown in FIG. 4B) to first position 62 (as shown in FIG. 4A) can move attachment members 256 from lumen 104 to lumen 102. Moving attachment member 256 from lumen 104 to lumen 102 can transition attachment member 256 from closed configuration 264 to open configuration 262. In open configuration 262, attachment member 252 can be decoupled from corresponding attachment member 256.

Movement of securing member 60 may be locked using a locking collar 72. Locking collar 72 could be configured for lateral movement relative to securing member 60 to limit longitudinal or rotational movement of securing member 60. Locking collar 72 also could be biased to move in and out of an indentation 73 to lock and unlock securing member 60. Other locking systems could include a lever, a cam lock, a rack and pawl, a knob, a thumb wheel and rack, or a worm gear.

As shown in FIG. 4B, an end 74 of locking collar 72 can engage indentation 73 configured to receive end 74. Indentation 73 could be mechanically coupled to securing member 60 such that engagement between end 74 and indentation 73 can limit relative movement between securing member 60 and handle 50. Other couplings between locking collar 72 and securing member 60 are also contemplated.

In some embodiments, locking collar 72 could be configured to lock securing member 60 in more than one position. As shown in FIGS. 4A and 4B, locking collar 72 can be configured to lock securing member 60 in second position 64. Locking securing member 60 can ensure that unwanted decoupling of control members 250, 255 does not occur.

As well as control members 250, 255, handle 50 and catheter 70 can be releasably coupled and locked. Handle 50 and catheter 70 can be coupled to ensure correct alignment of control members 250, 255. Also, handle 50 and catheter 70 can be lockable to limit a relative movement between handle 50 and catheter 70.

As shown in FIGS. 4A and 4B, handle 50 can include a handle connector 270 and catheter 70 can include a catheter connector 280, whereby connectors 270, 280 are configured to releasably couple. Handle connector 270 can include a key 92 configured to engage a keyway 274 of catheter connector 280. Alternatively, keyway 274 can be located on handle connector 270 and key 92 can be located on catheter connector 280. Other types of connectors 270, 280 could include a button, a lever, a cam, a rack and a pawl, a tab, or a thumb wheel and a gear. Handle 50 and catheter 70 could be connected using a collet, a ball and socket, a ¼ turn fastener, or a magnetic element.

Handle 50 and catheter 70 may be connected using straight-line movement or rotational movement. FIG. 5 depicts a partial cut away view of handle 50 and catheter 70 configured for straight-line connection. As shown, distal end 55 of handle 50 includes a straight keyway 274 and proximal end 75 of catheter 70 includes key 92. Distal end 55 also includes a thread 290 configured to threadably engage a threaded ring 292 located on proximal end 75. Threaded ring 292 may be rotatably coupled to proximal end 75.

Threaded ring 292 can be configured to rotate relative to catheter 70 and thread 290. Once key 92 has been moved longitudinally to a position within keyway 274, thread 290 may be rotated relative to threaded ring 292 to lock handle 50 and catheter 70. One or more keys 92 may be configured to engage one or more keyways 274. A latch, a clip, a thumbscrew, or other locking device may also be used to lock handle 50 and catheter 70.

Figure 6:
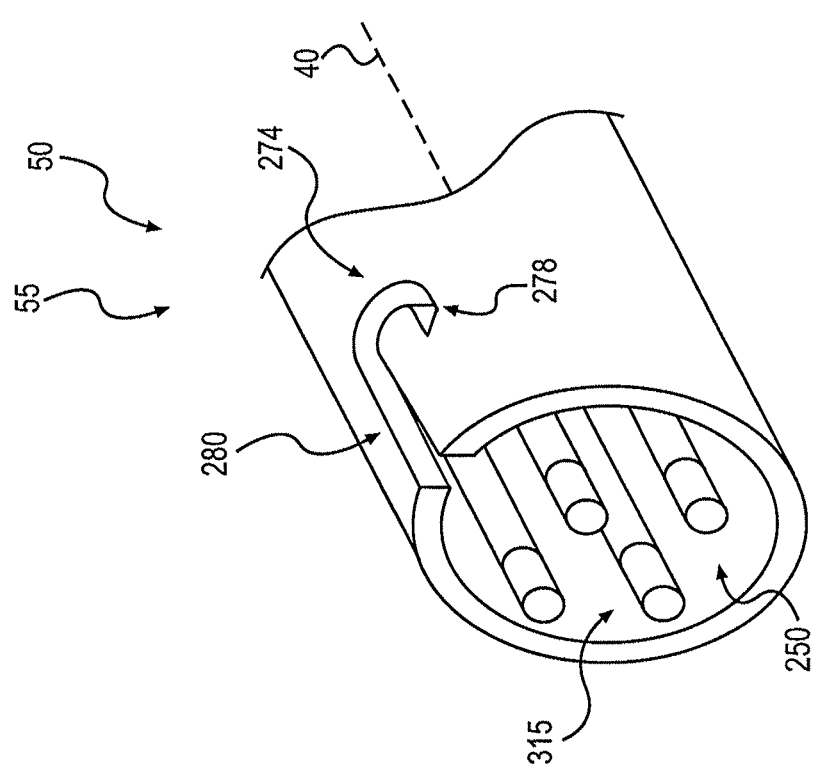
FIG. 6 is a perspective view of a portion of a handle, according to another exemplary embodiment of the invention.

FIG. 6 depicts distal end 55 of handle 50 configured for rotational connection with catheter 70. Handle 50 and catheter 70 can be connected using a bayonet or a luer lock type connection. In operation, key 92 located on proximal end 75 of catheter 70 may initially be placed within keyway 274 and moved longitudinally within keyway 274. Distal end 55 and proximal end 75 may then be rotated relative to each other about longitudinal axis 40 to move key 92 tangentially about distal end 55 of handle 50. Tangential movement of key 92 within keyway 274 can move key 92 to a locking position 278. When key 92 is located at locking position 278, a compressive force between handle 50 and catheter 70 may be required to release key 92 from keyway 274. To permit rotational coupling of handle 50 and catheter 70, control members 250 may each include a rotational attachment member 315.

FIGS. 7A and 7B depict rotational attachment member 315 located on handle control member 250 and a corresponding attachment member 340 located on catheter control member 255. Each attachment member 315, 340 can be configured to releasably couple using rotational movement of handle 50 relative to catheter 70. Attachment member 315 may also be located on catheter control member 255.

Attachment member 315 can include a cavity 350 configured to receive a head 370 of attachment member 340. Attachment member 340 can also include a neck 380 configured for placement within a distal opening 330 of cavity 350. Head 370 can be rotated into cavity 350 via a lateral opening 320 of cavity 350. For example, as key 92 is moved into locking position 278 of keyway 274, attachment member 340 can be moved into cavity 350, as shown in FIGS. 7A, 7B. This can ensure that distal end 55 of handle 50 and proximal end 75 of catheter 70 are coupled together as control members 250, 255 are coupled together.

FIG. 7B depicts attachment member 340 coupled to attachment member 315. As shown, head 370 can be located within cavity 350 to couple attachment members 340, 315. Longitudinal movement of handle control member 250 may be transferred to catheter control member 255 by coupling between head 370 and a wall 385 of attachment member 315. Distal opening 330 can be configured to receive neck 380 such that longitudinal movement can be transferred between control members 250, 255.

Figure 8:
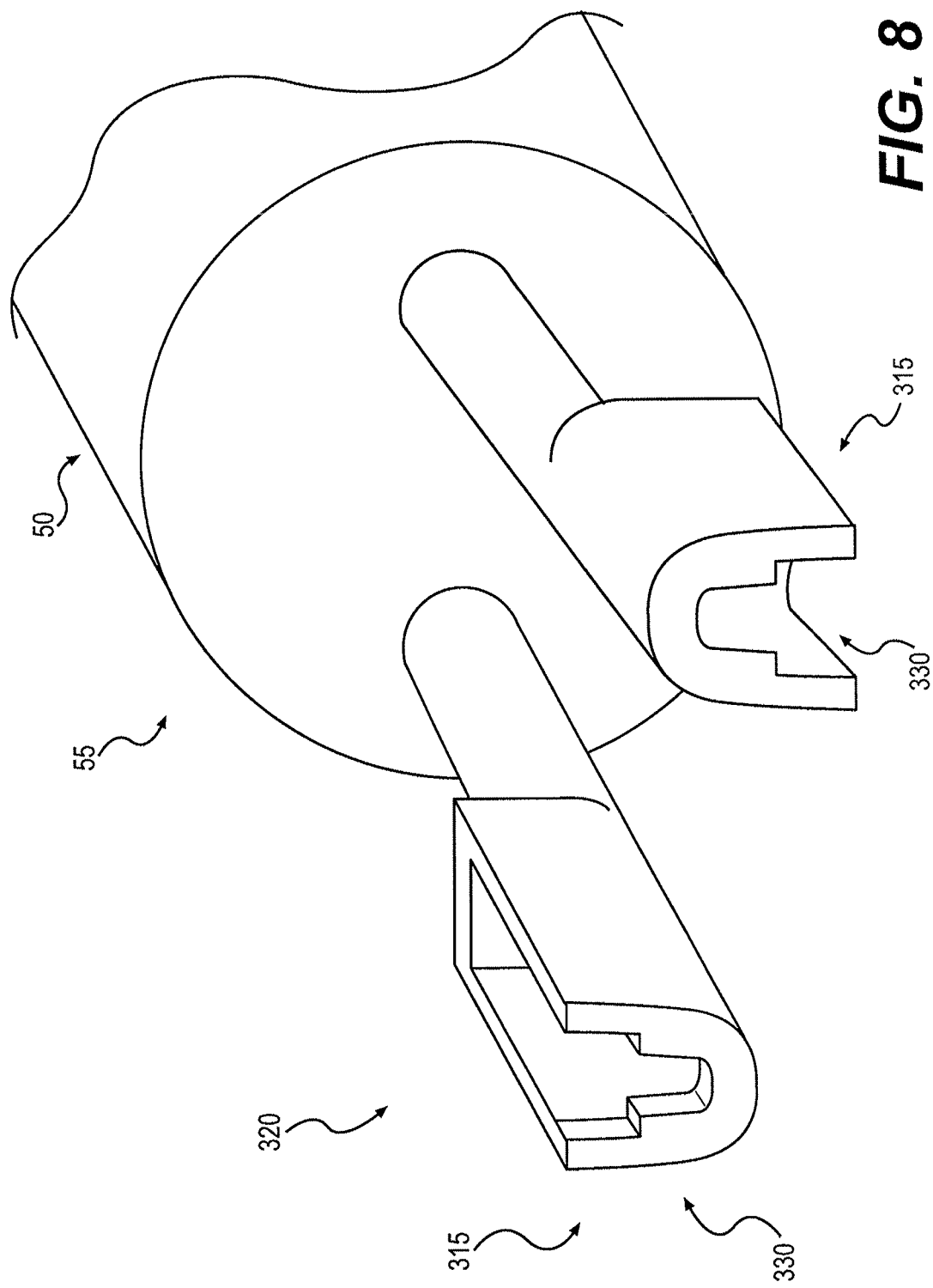
FIG. 8 is a perspective view of a portion of a handle showing attachment members, according to an exemplary embodiment of the invention.

FIG. 8 depicts distal end 55 of handle 50 having attachment members 315 configured for rotational coupling. As shown, attachment members 315 are configured to rotationally couple to corresponding attachment members (not shown). That is, handle 50 can be rotated clockwise relative to catheter 70 (not shown) to couple attachment members 315, 340 and rotated anticlockwise to decouple attachment members 315, 340. Lateral openings 330 can be oriented to receive multiple corresponding heads 370 simultaneously. Lateral openings 330 could also be configured to receive heads 370 using anticlockwise rotation.

It is also contemplated that attachment member 340 can include any shape configured to engage cavity 350. For example, head 370 could be "L" shaped and may pass into cavity 350 via only lateral opening 320. In such an embodiment, attachment member 315 may not require distal opening 330 and may only include lateral opening 320. One or more openings 320, 330 may also be variously shaped to permit passage of head 370 into cavity 350.

Figure 9A:
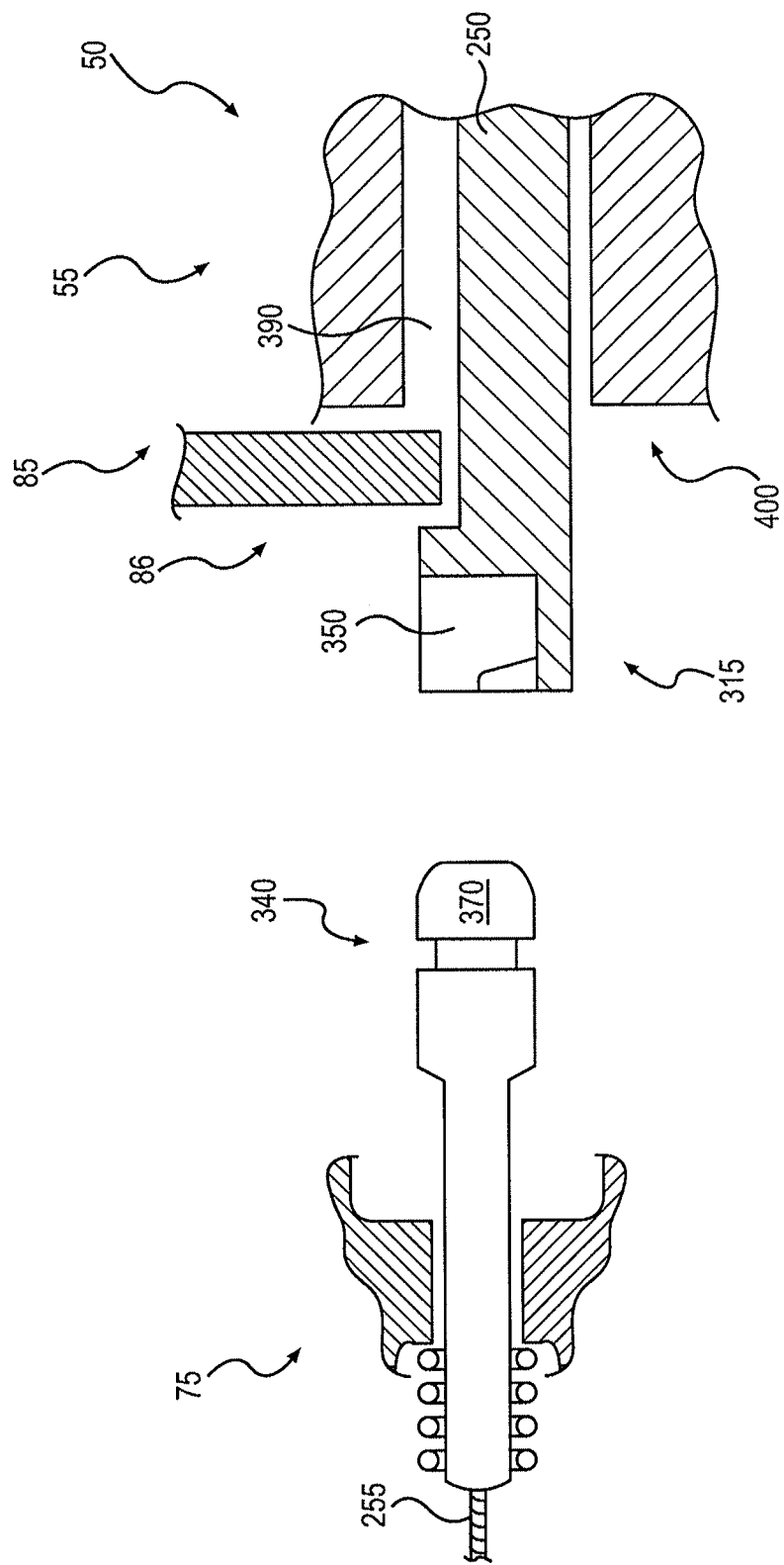
FIG. 9A is a side view of attachment members in a decoupled configuration, according to an exemplary embodiment of the invention.
Figure 9B:
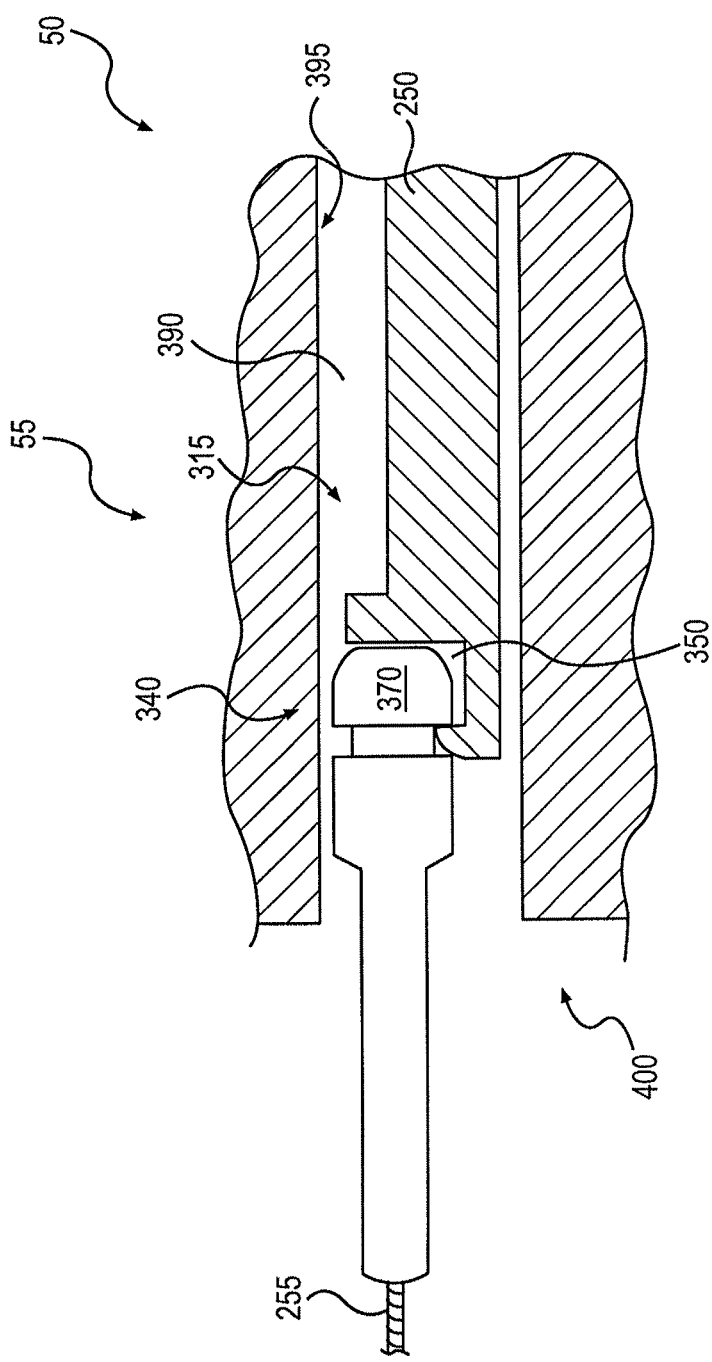
FIG. 9B is a side view of attachment members in a coupled configuration, according to an exemplary embodiment of the invention.

FIGS. 9A and 9B depict, respectively, attachment members 340, 315 as uncoupled and attachment members 340, 315 as coupled. In some embodiments, distal end 55 of handle 50 can include a lumen 390 configured to receive attachment member 315. Lumen 390 can be configured to at least partially maintain coupling between attachment members 340, 315. In other embodiments, catheter 70 can include lumen 390.

Initially, attachment member 315 can extend distally beyond a distal-most end 400 of lumen 390. Retaining member 85 may be configured to limit relative movement between attachment member 315 and lumen 390. As shown, retaining member includes a card 86 configured for placement between cavity 350 and distal-most end 400. Card 86 could be a plate, or other stopping structure. As previously explained, one or more other retaining members 85 could also be used.

With attachment member 315 extending beyond lumen 390, attachment member 340 can be moved rotationally to position head 370 within cavity 350. Once head 370 is properly positioned within cavity 350, retaining member 85 may be removed to permit longitudinal movement of engaged attachment members 315, 340 within lumen 390. As explained above, securing member 60 (not shown) can be configured to move attachment members 315, 340 longitudinally with respect to lumen 390.

FIG. 9B depicts coupled attachment members 315, 340 located within lumen 390. Lumen 390 can be configured to at least partially limit relative movement between attachment members 340, 315. For example, a surface 395 of lumen 390 may limit the lateral movement of attachment member 340 relative to attachment member 315. Lumen 390 can also be configured to limit the movement of head 370 relative to cavity 350. Such limited movement may maintain the coupling between attachment members 340, 315 to permit the transmission of movement or forces between control members 250, 255. To decouple attachment members 340, 315, they may be moved distally by securing member 60 to beyond distal-most end 400 of lumen 390, then rotated to move heads 370 out of cavities 350.

Figure 10:
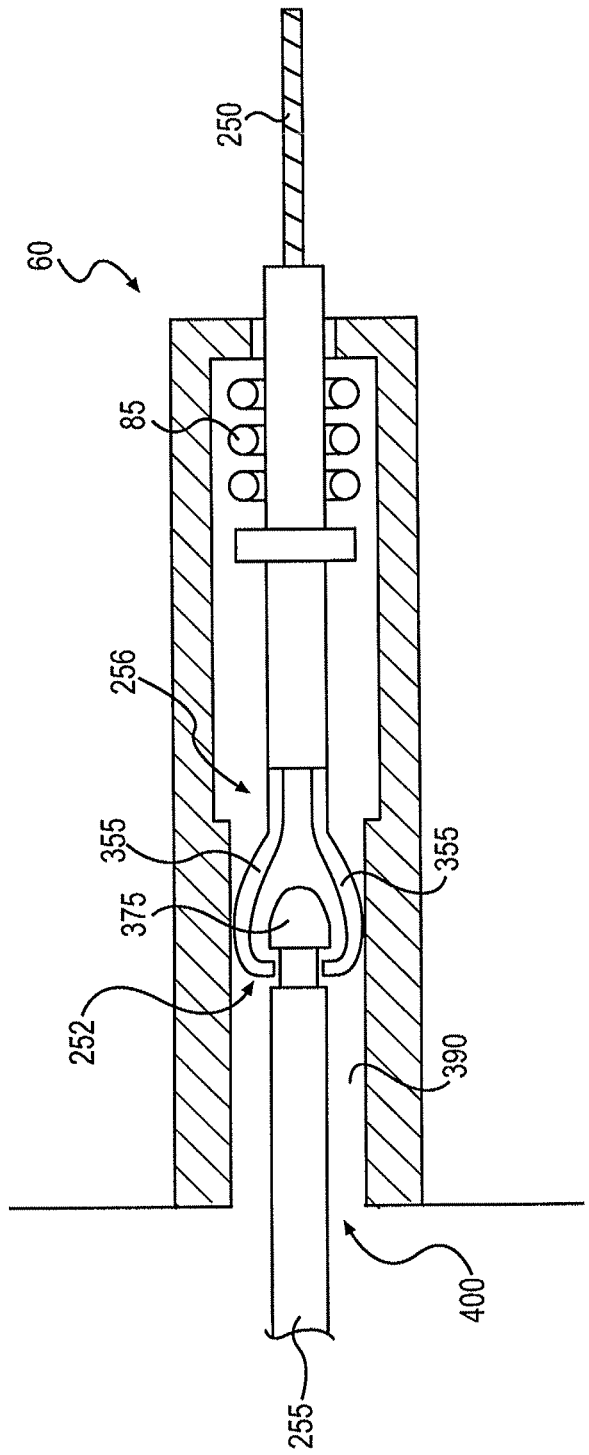
FIG. 10 is a side view of attachment members in a coupled configuration, according to an exemplary embodiment of the invention.

FIG. 10 depicts another embodiment of lumen 390 showing a straight-line connection between attachment members 252, 256. Attachment members 252, 256 are shown coupled within lumen 390. Similar to the rotational attachment shown in FIGS. 9A and 9B, attachment member 256 may be initially located distal of distal-most end 400 of lumen 390. Attachment member 256 located outside lumen 390 can be configured to assume open configuration 262 whereby arms 355 extend laterally to permit locating head 375 between open arms 355 (not shown).

Securing member 60 may then move distally (to the left) to move lumen 390 over attachment member 256, as shown in FIG. 10. Lumen 390 may be configured to transition attachment member 256 from open configuration 262 to closed configuration 264. Such movement can cause arms 355 to collapse about head 375 to couple attachment members 252, 256. During distal movement of securing member 60, retaining member 85 can provide a slight tensile force to maintain positioning of attachment member 256 against attachment member 252.

To decouple attachment members 256, 252, securing member 60 can move proximally (to the right) to move arms 355 out of lumen 390. Once beyond distal-most end 400, arms 355 can reopen to permit removal of head 375 from between arms 355. Coupling and decoupling attachment member 252, 256 can releasably couple control members 250, 255.

Figure 11A:
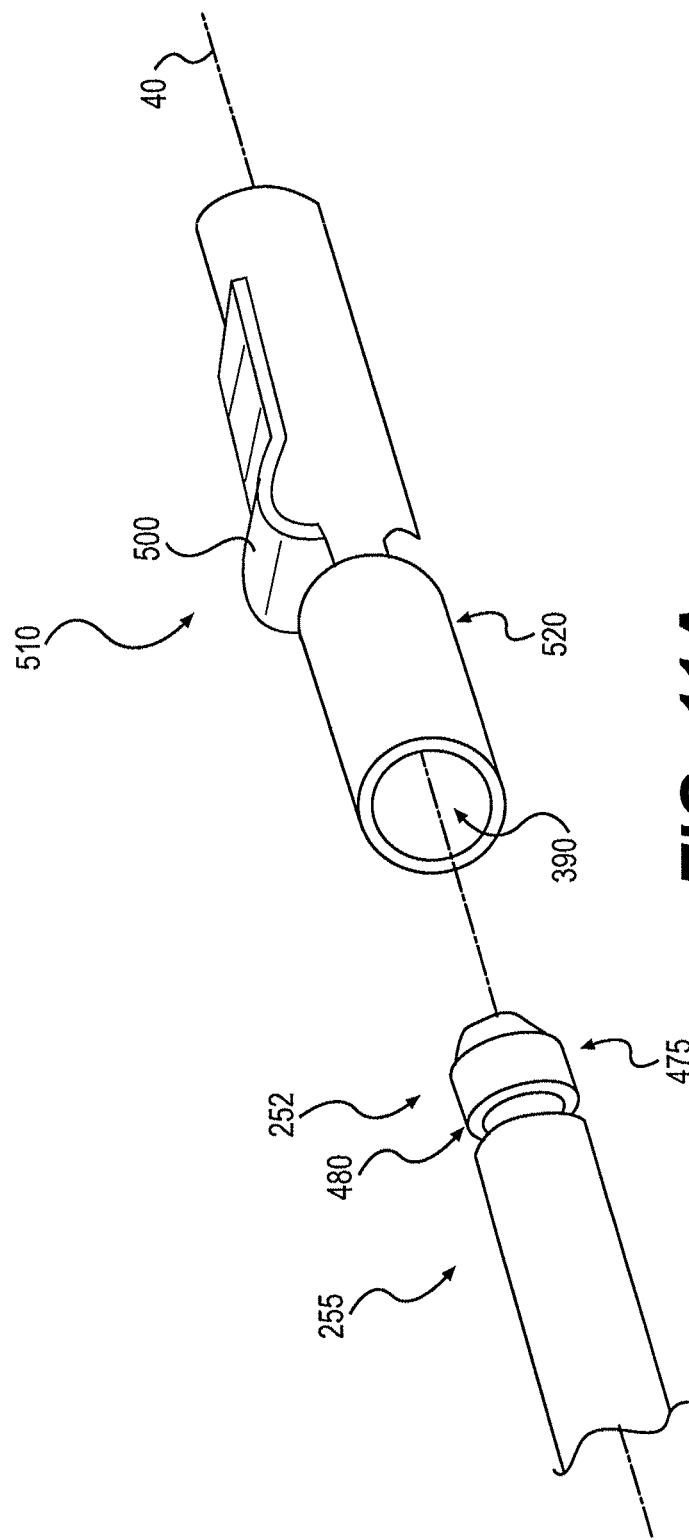
FIG. 11A is a side view of attachment members in a decoupled configuration, according to an exemplary embodiment of the invention.

FIGS. 11A and 11B depict another embodiment of lumen 390 showing a straight-line connection between attachment member 252 and corresponding attachment member 510. Attachment member 252 can be coupled to catheter control member 255 and can include a neck 480 and a head 475. Attachment member 510 can be coupled to handle control member 250 (not shown) and can include a clip 500 configured to move relative to a tubular member 520. Tubular member 520 can be configured to receive attachment member 252.

Clip 500 can be configured to assume an open configuration and a closed configuration to releasably couple attachment members 510, 252. In some embodiments, clip 500 may be moved relative to tubular member 520 using securing member 60 (not shown). For example, clip 500 may move along longitudinal axis 40 relative to tubular member 520. This longitudinal movement may cause clip 500 to open or close.

FIG. 11B depicts clip 500 in a closed configuration. As shown, two clip arms 550 can extend through one or more slots 530 of tubular member 520 to engage neck 480 of attachment member 252. Such engagement can limit longitudinal movement between attachment members 510, 252. To decouple attachment members 510, 252, clip 500 could be moved longitudinally relative to tubular member 520. The longitudinal movement could cause arms 550 to open as they are removed from within tubular member 520. Other types of attachment members could also be configured for releasable coupling.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device comprising:
a handle body having a proximal end and a distal end, the handle body configured to releasably couple to a shaft;
an actuator coupled to the handle body; and
a handle control member coupled to the actuator, wherein the actuator is configured to move relative to the handle body to move the handle control member relative to the handle body, wherein a distal end of the handle control member includes an attachment member for releasably coupling the distal end of the handle control member to a proximal end of a shaft control member within the shaft, wherein the handle control member includes a retaining member, wherein the retaining member is configured to transition between a first configuration, in which the handle control member has a first length, and a second configuration, in which the handle control member has a second length, shorter than the first length, wherein the retaining member is biased into the first configuration, and wherein the retaining member includes at least one of a spring, a button, a lever, or a latch.

2. The device of claim 1, wherein the handle control member includes at least one of a cable, a wire, a thread, a coil, or a ribbon.

3. The device of claim 1, wherein the actuator includes at least one of a knob, a dial, a lever, or a rotatable grip.

4. The device of claim 1, wherein the attachment member (a) includes a protrusion extending radially outward from a longitudinal axis of the handle control member or (b) defines a cavity.

5. The device of claim 1, further comprising the shaft, wherein the attachment member is a first attachment member, wherein the shaft control member includes a second attachment member at a proximal end of the shaft control member.

6. The device of claim 5, wherein one of the first attachment member or the second attachment member includes a protrusion and an other of the first attachment member or the second attachment member defines a cavity for receiving the protrusion.

7. The device of claim 6, wherein the cavity is configured to be coupled to the protrusion via (a) axial movement of the protrusion relative to the cavity, (b) rotational movement of the protrusion relative to the cavity, or (c) a clip configured to selectively engage the protrusion.

8. The device of claim 1, further comprising a lock positioned at the distal end of the handle body, wherein the lock is movable relative to the handle body, and wherein the lock is configured to secure the shaft to the handle body.

9. The device of claim 1, wherein the distal end of the handle control member is proximal of the distal end of the handle body.

10. The device of claim 1, wherein the handle control member is a first handle control member, the attachment member is a first attachment member, and the shaft control member is a first shaft control member, further comprising a second handle control member terminating at a distal end, wherein the distal end of the second handle control member includes a second attachment member for releasably coupling the distal end of the second handle control member to a proximal end of a second shaft control member within the shaft.

11. The device of claim 10, wherein the first attachment member has a first shape to complement the first shaft control member, and wherein the second attachment member has a second shape, different from the first shape, to complement the second shaft control member.

12. A device comprising:
a handle body having a proximal end and a distal end, the handle body configured to releasably couple to a shaft; and
a handle control member configured to move relative to the handle body in order to articulate a portion of the shaft when the shaft is releasably coupled to the handle body, wherein a distal end of the handle control member includes an attachment member for releasably coupling the distal end of the handle control member to a proximal end of a shaft control member within the shaft, wherein the handle control member includes a retaining member, wherein the retaining member is configured to transition between a first configuration, in which the handle control member has a first length, and a second configuration, in which the handle control member has a second length, shorter than the first length, wherein the retaining member is biased into the first configuration, and wherein the retaining member includes at least one of a spring, a button, a lever, or a latch.

13. The device of claim 12, further comprising the shaft, wherein the attachment member is a first attachment member, wherein the shaft control member includes a second attachment member at a proximal end of the shaft control member.

14. The device of claim 13, wherein one of the first attachment member or the second attachment member includes a protrusion, and an other of the first attachment member or the second attachment member defines a cavity for receiving the protrusion.

15. The device of claim 14, wherein the cavity is configured to be coupled to the protrusion via (a) axial movement of the protrusion relative to the cavity, (b) rotational movement of the protrusion relative to the cavity, or (c) a clip configured to selectively engage the protrusion.

16. A device comprising:
a handle body having a proximal end and a distal end, the handle body configured to releasably couple to a shaft; and
a handle control member configured to move relative to the handle body, wherein a distal end of the handle control member includes an attachment member for releasably coupling the distal end of the handle control member to a proximal end of a shaft control member within the shaft, wherein the attachment member includes at least one of a protrusion or a cavity, wherein the handle control member includes a retaining member, wherein the retaining member is configured to transition between a first configuration, in which the handle control member has a first length, and a second configuration, in which the handle control member has a second length, shorter than the first length, wherein the retaining member is biased into the first configuration, and wherein the retaining member includes at least one of a spring, a button, a lever, or a latch.

17. The device of claim 16, wherein the handle control member is coupled to an actuator, and wherein movement of the handle control member is configured to articulate a portion of the shaft when the shaft is releasably coupled to the handle body.

18. The device of claim 15, wherein the handle control member is a first handle control member, the attachment member is a first attachment member, and the shaft control member is a first shaft control member, further comprising a second handle control member terminating at a distal end, wherein the distal end of the second handle control member includes a second attachment member for releasably coupling the distal end of the second handle control member to a proximal end of a second shaft control member within the shaft, wherein the first attachment member has a first shape to complement the first shaft control member, and wherein the second attachment member has a second shape, different from the first shape, to complement the second shaft control member.

\* \* \* \* \*